United States Patent
Bartholomew

(10) Patent No.: US 6,936,210 B2
(45) Date of Patent: Aug. 30, 2005

(54) WAVE MOLDING METHOD AND APPARATUS FOR MANUFACTURING CANNULAE

(75) Inventor: Ross Bartholomew, Orem, UT (US)

(73) Assignee: Edwards Lifesciences Corporation, Irvine, CA (US)

(*) Notice: Subject to any disclaimer, the term of this patent is extended or adjusted under 35 U.S.C. 154(b) by 404 days.

(21) Appl. No.: 10/172,668

(22) Filed: Jun. 14, 2002

(65) Prior Publication Data

US 2003/0230822 A1 Dec. 18, 2003

(51) Int. Cl.⁷ .......................... B29C 41/08; B28B 1/38; B28B 1/32; B28B 1/02
(52) U.S. Cl. ...................... 264/294; 264/301; 264/303; 264/309; 264/310
(58) Field of Search ................................. 264/294, 301, 264/303, 309, 310

(56) References Cited

U.S. PATENT DOCUMENTS

| | | | |
|---|---|---|---|
| 1,974,990 A | 2/1934 | Hopkinson | |
| 2,081,533 A | 5/1937 | Ford et al. | |
| 3,459,578 A | 8/1969 | Laulan | |
| 3,802,908 A | 4/1974 | Emmons | |
| 5,116,652 A | 5/1992 | Alzner | |
| 5,496,294 A | 3/1996 | Hergenrother et al. | |
| 5,527,276 A | 6/1996 | Bruce | |
| 5,537,729 A | 7/1996 | Kolobow | |
| 5,630,806 A | 5/1997 | Inagaki et al. | |
| 5,722,395 A | 3/1998 | Kolobow | |
| 5,785,998 A | 7/1998 | Kolobow | |
| 5,863,366 A | 1/1999 | Snow | |
| 5,879,342 A | 3/1999 | Kelley | |
| 5,885,251 A | 3/1999 | Luther | |
| 5,947,940 A | 9/1999 | Beisel | |
| 6,004,310 A | 12/1999 | Bardsley et al. | |
| 6,030,371 A | 2/2000 | Pursley | |
| 6,053,903 A | 4/2000 | Samson | |
| 6,280,788 B1 | 8/2001 | Brinckmann | |

*Primary Examiner*—Stephen J. Lechert, Jr.
(74) *Attorney, Agent, or Firm*—Edwards Lifesciences

(57) ABSTRACT

A method of making a cannula includes providing a plurality of polymer reservoirs with each reservoir containing a polymer material and providing a nozzle mounted within each reservoir of the plurality of reservoirs. The method further includes one or more of preheating the mandrel, generating a polymer material wave from each nozzle, rotating the mandrel over the nozzles to form an initial coat on the mandrel, curing the initial coat, depositing a reinforcing material around a selected section of the mandrel and ensuring that the reinforcing material is held in place at the selected section of the mandrel. The method further includes rotating each section of the mandrel over a selected nozzle to form an additional coat, curing the additional coat, and removing the tubular structure from the mandrel.

26 Claims, 10 Drawing Sheets

WAVE MOLDING METHOD AND APPARATUS FOR MANUFACTURING CANNULAE

FIELD OF THE INVENTION

The present invention is related generally to manufacturing cannulae and more specifically to a wave molding process for manufacturing various sizes and configurations of cannulae.

BACKGROUND OF THE INVENTION

A cannula is basically a small tube made for insertion into a body cavity or into a duct or vessel for infusion, draining and monitoring. Cannulae also include various types of specialized tubing that are used in the surgical field to transport blood from the heart to a cardiopulmonary pump and oxygenator, and to return the blood to the circulatory system. While there are standard configurations of cannulae, many are custom-designed to suit the individual surgeon's requirements. Leading corporations produce more than 1,200 types of cannulae and accessories to facilitate cardiopulmonary bypass. More recent developments include a line of cannulae to facilitate vacuum-assisted venous drainage during cardiopulmonary bypass and dispersion aortic cannulae, which are used to reduce the pressure of blood flow returning to the body through the aorta.

Cannulae and catheters are manufactured by utilizing various different processes. U.S. Pat. Nos. 3,802,908, 5,537,729, 5,722,395, and 5,785,998 describe some of the current manufacturing processes that may be utilized in producing cannulae and catheters and are incorporated herein by reference. Pat. No. 3,802,908 issued to Emmons discloses a process for forming a multi-layer resinous coating by applying flowable heat softened resinous material directly to the external surface of a rotating cylindrical pipe at ambient temperature. U.S. Pat. Nos. 5,537,729, 5,722,395, and 5,785,998 issued to Kolobow disclose a method of making ultra thin walled wire reinforced endotracheal tubing. Kolobow discloses thin walled tubing manufactured of a polymeric material having a spring wire material incorporated therewith. Utilization of the spring wire material in combination with the polymeric material results in reduced wall thickness, which decreases the resistance to airflow through the endotracheal tubing. The endotracheal tubing is made by depositing a dissolvable polymeric material on a rotating mandrel in successive layers. A spring material is also applied around the mandrel to produce the ultra thin walled wire reinforced endotracheal tubing. By controlling the rate of deposition of the polymeric material along the length of the mandrel, different wall thicknesses of tubing may be achieved.

During an extrusion process, polymer material is forced through a die. Almost any solid or hollow cross-section may be produced by utilizing the extrusion process. After a first layer is applied over the mandrel utilizing the extrusion process, a wire is wrapped around the first layer. Once wrapped with the wire, a second layer is extruded over the wire to produce a cannula that is wire-reinforced. Once the plastic reinforced tube is extruded, it is stripped from the mandrel, and cut in a desired length. Additional pieces, depending on the specific design of the cannula, are molded, welded, or connected to the plastic reinforced tube to create a cannula. These various process steps can be very expensive because of small lots of production and varying sizes of cannulae. Most of the cost savings with the extrusion process come from being able to run thousands of feet at a time.

A dipping process is commonly used with silicon and other types of thermal set material. U.S. Pat. No. 5,885,251 issued to Luther discloses a dipping process associated with producing a catheter and is incorporated herein by reference. The catheter is formed by a sequential mandrel dip process. More particularly, a rigid tip portion may be formed by dipping a mandrel into a solubilized softenable material and allowing the softenable material to dry on the mandrel. The softenable material is preferably hydrated from the mandrel and the desired length for the distal tip portion is cut off. This distal portion is then applied to and dried on a secondary dipping mandrel and a length of flexible catheter is inserted over the mandrel such that the catheter abuts the softenable distal portion. The softenable portion and the portion of flexible catheter are then dipped into a liquid polymer such that the two portions are solvent welded together and an outer layer of polymer is deposited thereover. Thus a contiguous assembly is formed by bonding the softenable material to the distal end of the flexible catheter. The assembly is then allowed to dry and the dipped softenable tip portion is trimmed to exhibit a profile that facilitates insertion into a patient. The mandrel is subsequently removed from the assembly of the catheter and the softenable portion such that a continuous lumen is formed within both portions. A needle cannula is then inserted through the wall of the catheter and extended axially through the length of the catheter such that its sharp tip extends outwardly beyond the softenable end of the catheter.

Although the dipping process may be desirable in certain situations, dipping is sometimes not a desirable option for cannulae manufacturing because of excessive cost, extended process cycle time, many secondary steps to make a final product, and a need for on-going monitoring and adjustments during the manufacturing process. These variables and additional process steps significantly increase the cost of the product.

SUMMARY OF THE INVENTION

The present invention provides a method for making a cannula utilizing wave molding. The method includes one or more of the following steps. Generating a polymer material wave, rotating a mandrel in the polymer material wave to form a coat of the polymer material around the mandrel thereby forming a tubular structure, and removing the tubular structure from the mandrel.

In one embodiment, the method further includes preheating the mandrel. In another embodiment, the rotating step further includes rotating the mandrel in the polymer material wave to form an initial coat on the mandrel, curing the initial coat, and depositing a reinforcing material around a selected section of the mandrel. Known mechanical methods are used to ensure that the reinforcing material is held in place at the selected section of the mandrel when the mandrel is rotated over the polymer material solution. The rotating step further includes rotating the coated mandrel and the reinforcing material in the polymer material to form an additional coat of polymer material over the reinforcing material and the initial coat to form the tubular structure, and curing the additional coat.

The method further includes performing additional steps that may include finishing, punching, cutting, joining, connecting, molding, hardening, bending, marking, and painting to produce the cannula out of the tubular structure.

In yet another embodiment, a method of making a cannula having a plurality of sections with different properties and/or tube thicknesses is provided. The method includes providing a plurality of polymer reservoirs with each reservoir containing a polymer material, and providing a nozzle mounted within each reservoir of the plurality of reservoirs. The method further includes pre-heating a mandrel having a plurality of sections, generating a polymer material wave from each nozzle, rotating the mandrel over the nozzles to form a coating on the mandrel, and curing the coating. Each reservoir can be provided with a different polymer material, respectively, to provide a cannula having different properties along its length. Alternatively, each reservoir may have the same polymer material, but one section of mandrel is placed in the wave of one reservoir for a different period of time than another section of mandrel in another reservoir, to produce a cannula having different thicknesses along its length.

The method can also include depositing a reinforcing material onto and around a selected section of the mandrel, and ensuring that the reinforcing material is held in place at the selected section of the mandrel. The method further includes rotating each section of the mandrel over a selected nozzle, wherein each nozzle forces the polymer material solution around the selected section of the mandrel that is being rotated thereby forming a final coat over the mandrel to form a tubular structure with varying properties including the hardness. The final coat is then cured, and additional steps can be performed to produce the cannula having a plurality of sections with different properties. In one embodiment, the reservoirs contain polymer material solutions having different properties from each other.

Each polymer material is selected based on the cannula to be produced and the type of strength/hardness desired for each section of the cannula. The polymer material is pumped from each reservoir to each respective nozzle to generate polymer material waves. Once the reinforcing material is deposited, the reinforced material is held in place over the selected section of the mandrel manually or by a mechanical device. The reinforced material may be a stainless steel spring, a stainless steel spring in an uncoiled configuration, a spiral thin walled extruded tube made out of a plastic material, or a braided configuration of stainless steel, plastic, or other fiber. The method further permits the production of tubular structures with varied dimensions and strengths by regulating the type of the nozzle, the type of the mandrel, the rotating step, the preheating in the initial coat step, the preheating in the final coat step, the selection of the reinforcing material, and the selection of the polymer material.

The apparatus also includes an actuator to move the mandrel across the nozzle. Alternatively, or in addition to the actuator, a platform for the reservoir(s) and/or nozzle(s) is provided to move the polymer wave along the mandrel.

The apparatus further includes a heater to apply heat to the mandrel at pre-determined stages of manufacturing to cure the polymer material to produce a tubular structure. The heater is further configured to pre-heat the mandrel, and to cure an initial coat as well as a final coat over the mandrel by utilizing an induction coil. The apparatus may include other methods known in the art instead of the induction coil to apply heat. The polymer material solution utilized in the apparatus may be plastisol, silicone, organisol, ridgisol, or urethane. Depending on the type of the material selected, pre-heat or cure may not be required because the solvent is evaporated leaving polymer as a desired layer.

In yet another embodiment, the apparatus is configured to produce the cannula having two or more sections with different properties. In such a situation, the other components of the apparatus, such as a number of nozzles, a number of reservoirs, a mechanical device, an actuator and a type of polymer material solutions are modified depending on the type of the cannula that is being produced.

BRIEF DESCRIPTION OF THE DRAWINGS

The invention is best understood from the following detailed description when read in conjunction with the accompanying drawings. Like numerals denote like features throughout the specification and drawings. Included are the following figures.

DETAILED DESCRIPTION

The present invention relates to an apparatus and a method for manufacturing cannulae and more specifically to a wave molding process for manufacturing various sizes and configurations of cannulae that reduces unit cost and improves performance of cannulae.

Figure 1:
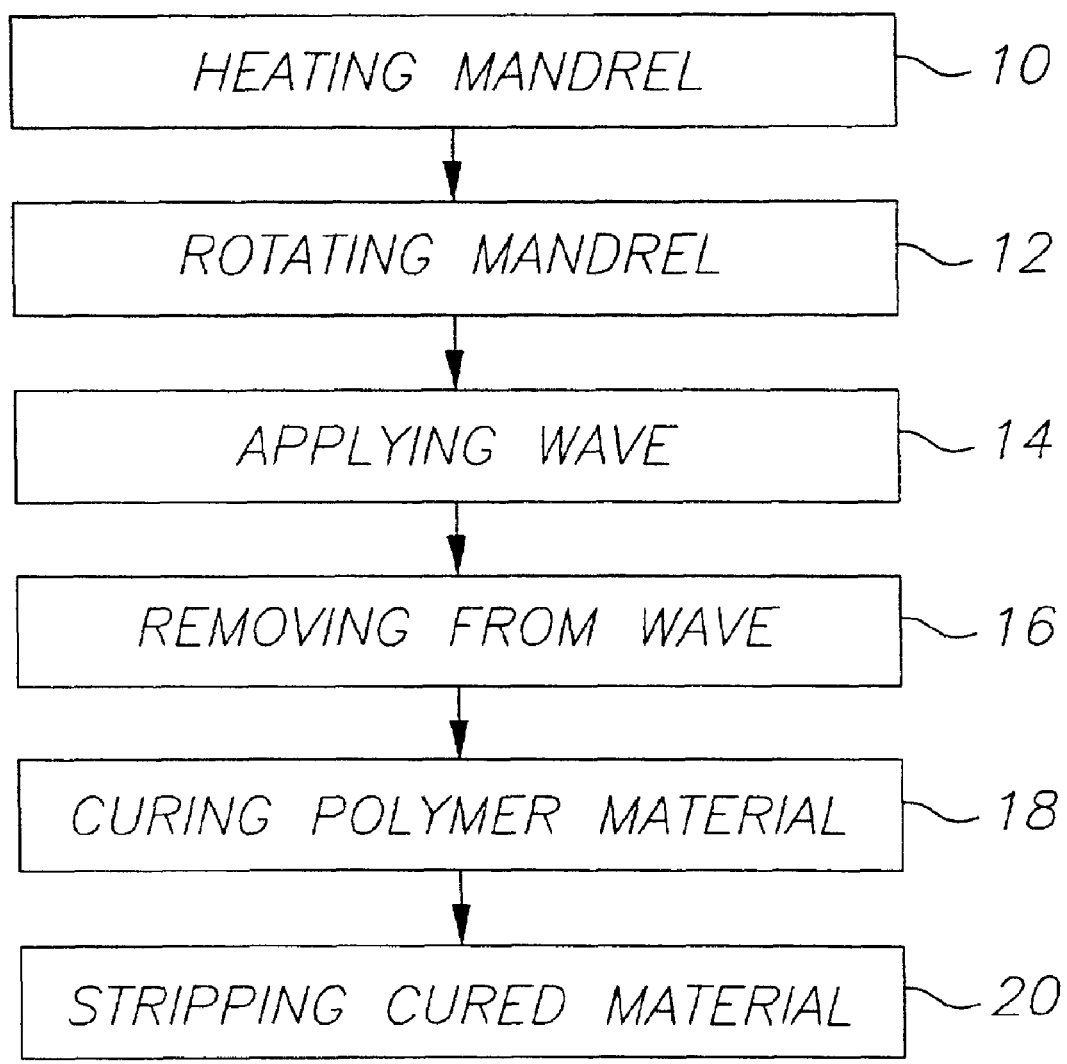
FIG. 1 is a flowchart of manufacturing steps for one embodiment of the present invention.

With reference to FIG. 1, a method of manufacturing cannulae using a wave molding process includes heating a mandrel (step 10), rotating the mandrel (step 12), placing the rotating mandrel into a wave of polymer material (step 14), removing the mandrel from the wave of polymer material (step 16), curing the polymer material (step 18) and stripping the cured polymer material from the mandrel (step 20).

Figure 2:
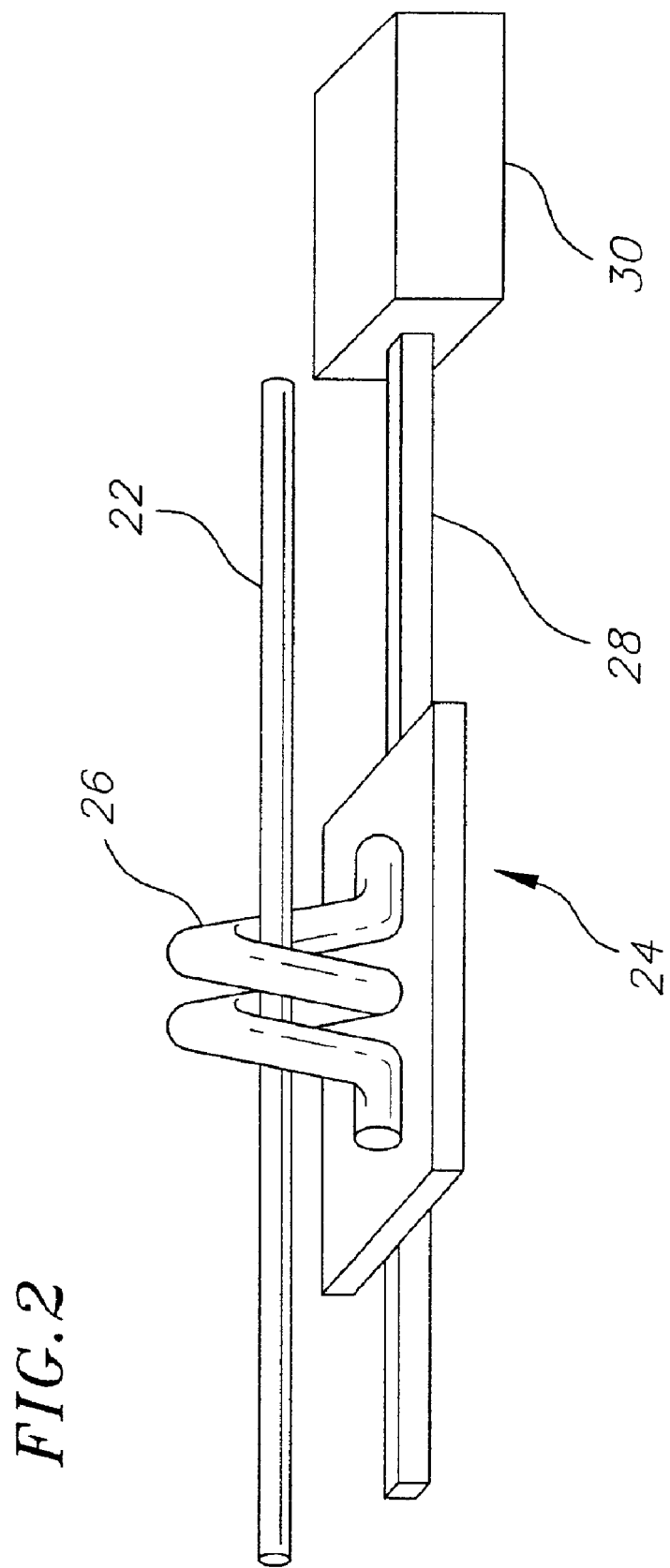
FIG. 2 is a schematic representation of a heater for use in the present invention.

With reference to FIG. 2, an elongated mandrel 22 is heated using a heating apparatus 24 that includes an induction coil 26 mounted to a rail 28. The rail is moveable to permit the induction coil to move along the mandrel to heat selected areas along the length of the mandrel. The induction coil and rail are controlled by a controller 30 that is programmed as desired to control the movement of the rail as well as the power output of the induction coil. When the induction coil passes over the mandrel, the mandrel heats up depending on the power output of the coil.

Instead of the induction coil, the heating apparatus may be any other commercially available apparatus to supply heat to the mandrel, for example, a radiant heater, a conduction heater, or a convection heater. It will be appreciated by those skilled in the art that instead of moving the heating apparatus along the mandrel, a mechanism can be provided to move the mandrel along the heating mechanism and heating means may be provided with no movement of either mandrel or heater.

Figure 3:
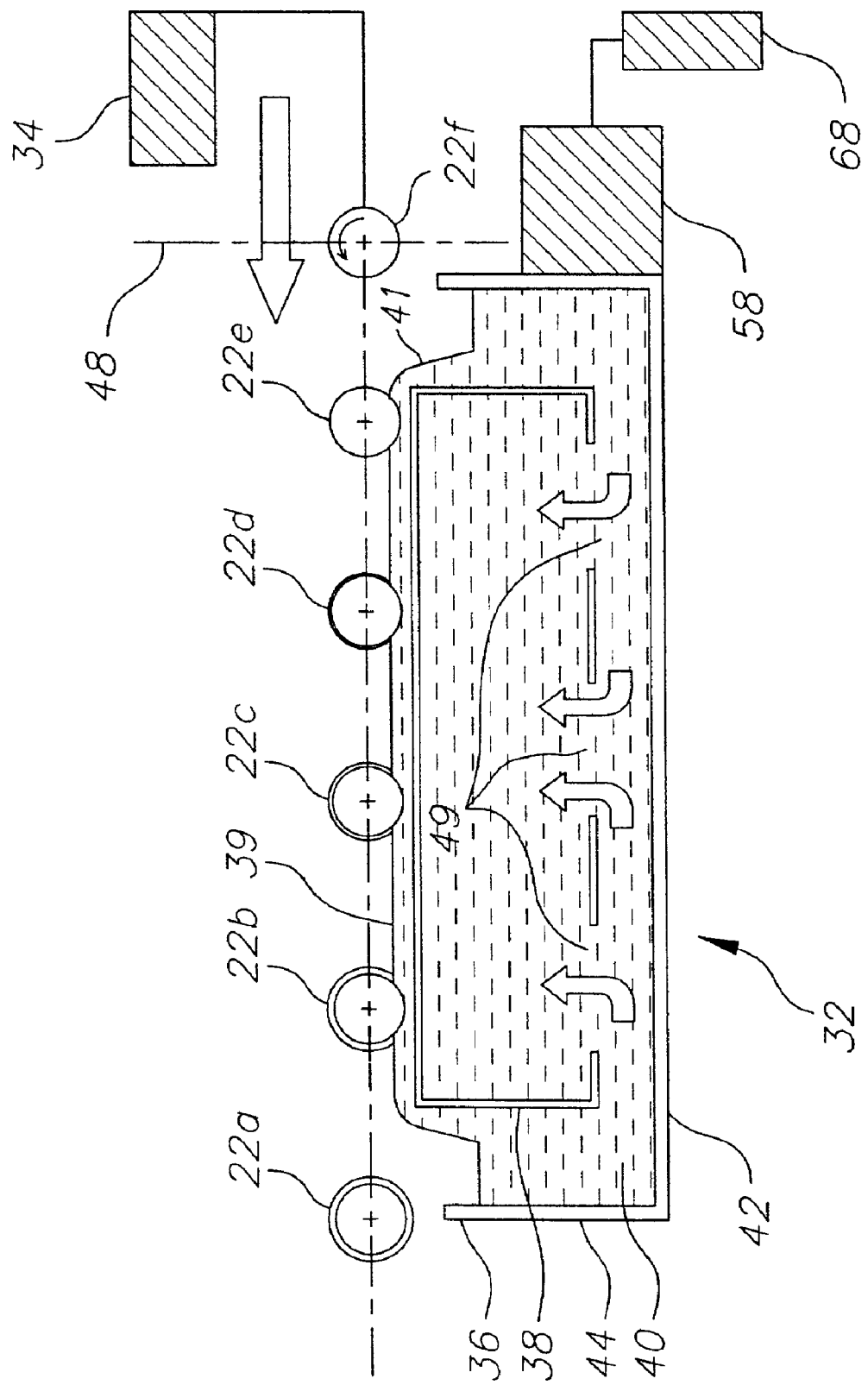
FIG. 3 is a front view of an embodiment of the apparatus for use in the present invention wherein the nozzle is stationary and a plurality of mandrels are rotated over the length of the reservoir at a pre-determined speed to ensure that the complete sections of the mandrels contact the polymer wave for the same amount of time producing consistent, uniform dimensions over the entire cannula.
Figure 4:
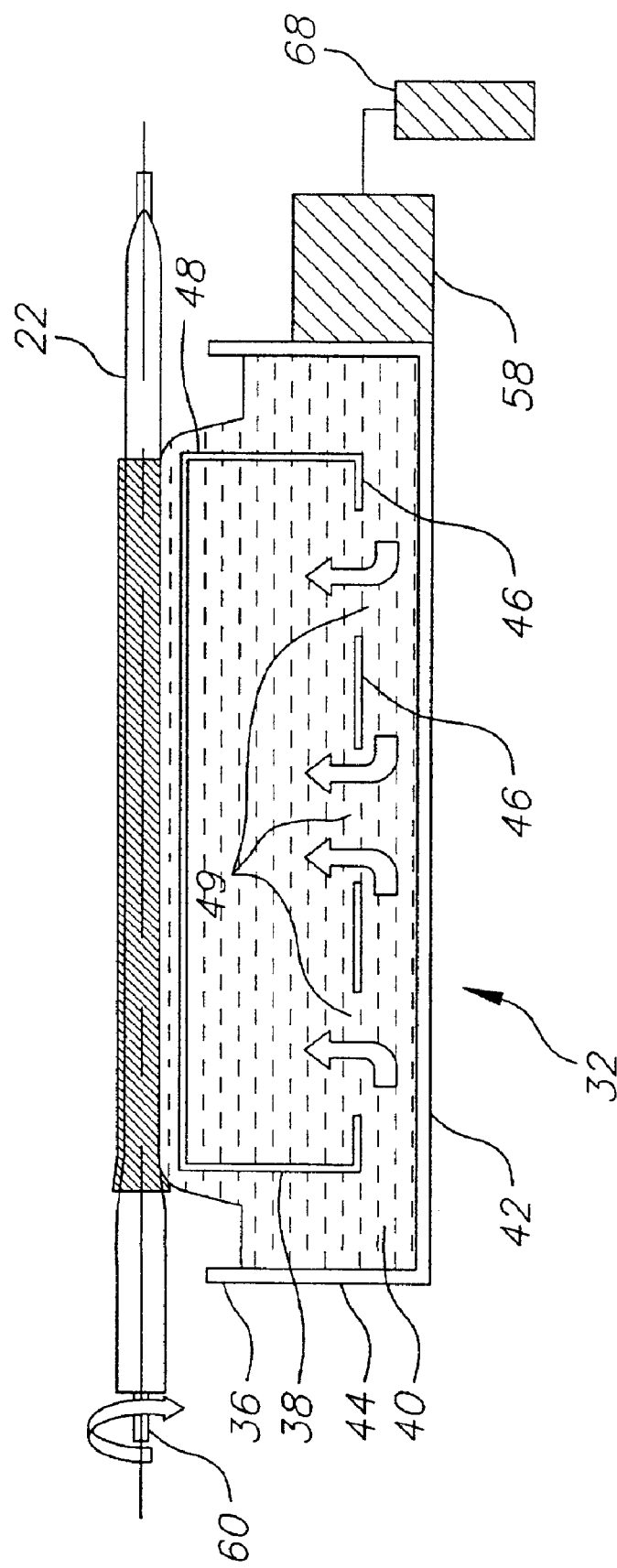
FIG. 4 is a side view of the embodiment of FIG. 3.

With reference to FIGS. 3 and 4, a wave molding apparatus 32, includes a reservoir 36, a nozzle 38 located in the reservoir for producing a wave 39, and a lathe 34 for rotating the mandrel or a plurality of mandrels. The lathe 34 is indicated schematically because mechanisms for rotating the mandrel are well known in the art. Several mandrels 22a, 22b, 22c, 22d, 22e, and 22f are rotated over the length of the wave 39 at a pre-determined speed to ensure that the same sections of the mandrels 22a, 22b, 22c, 22d, 22e, and 22f contact the polymer material for the same amount of time producing consistent, uniform dimensions over each cannula.

Figure 5:
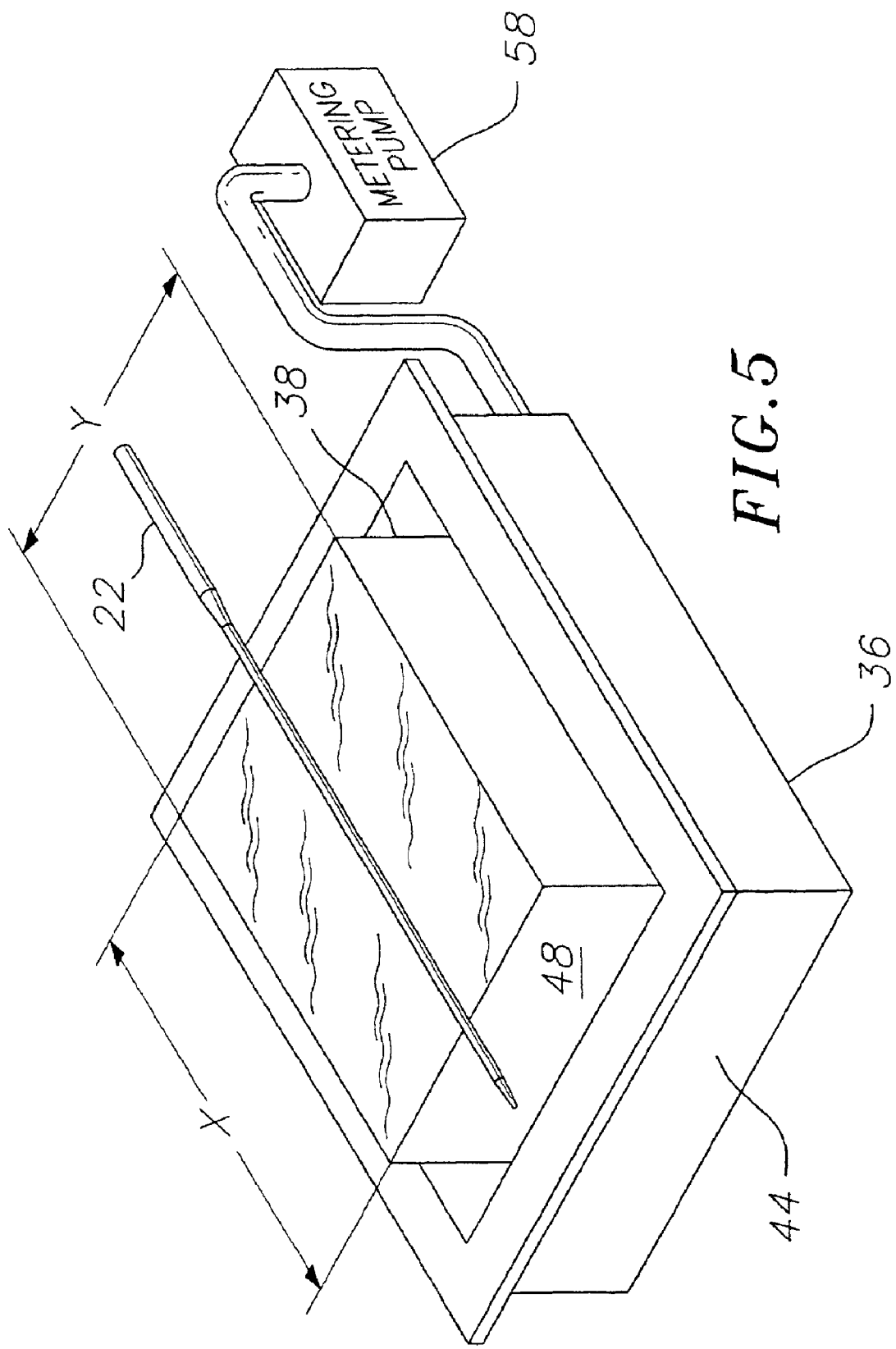
FIG. 5 is a perspective view of the embodiment of FIG. 3.

Reservoir 36 is any suitable container for holding a volume of polymer material 40 to be used to form the cannulae. The reservoir includes a base 42 and a plurality of walls 44. With reference to FIG. 5, the reservoir walls 44 define a square shape, although other shapes are contemplated. If desired the reservoir 36 also includes an independent heater (not shown) to maintain the polymer material in the reservoir at a pre-determined temperature depending on the type of the application. For example, an independent heater can be mounted underneath the reservoir to provide sufficient heat to the reservoir to maintain the polymer material at a constant temperature for process consistency. Alternatively, or in addition to the heater, a cooling system (not shown) can be provided to maintain the reservoir at a constant temperature for process consistency.

The nozzle 38 having a base 46 and a plurality of walls 48 is mounted inside the reservoir. Several openings 49 are provided through the base of the nozzle to supply polymer material from the reservoir into the nozzle. A metering pump, shown schematically at 58, pumps the polymer material up through the nozzle to produce a flat uniform wave of polymer material that overflows the walls of the nozzle back into the reservoir. Referring also to FIG. 5, the walls 48 of the nozzle are higher than the walls of 44 of the reservoir. It is believed that designs for reservoirs, nozzles and pumps similar to those used in wave soldering applications in the electronic/semiconductor industries would be suitable for manufacturing the wave molding apparatus of the present invention with suitable modifications to accommodate polymer materials and the manufacture of cannulae.

With reference again to FIG. 5, the nozzle has a width X and a length Y. The width X determines the portion of the mandrel to be coated with polymer material and the length Y determines the duration of time that the mandrel remains in contact with the wave (depending on the relative movement between the mandrel and the wave molding apparatus).

Relative movement between the rotating mandrel and the wave molding apparatus is required to bring the mandrel into contact with the wave of polymer material. Such a mechanism for moving the mandrel, or a plurality of mandrels, or for moving the wave molding apparatus, are readily designed by those skilled in the art, e.g., by drive gearing or rack and pinion gearing. With reference to FIG. 4, a rail 60 is schematically shown for moving the mandrel, or a plurality of mandrels (see FIG. 3) horizontally across the wave. In addition, instead of moving a rotating horizontal mandrel across the top of the wave, the rotating mandrel can be placed into contact with a side portion 41 of the wave. Alternatively, the wave molding apparatus can be moved or both the mandrels and the wave molding apparatus can be moved. For example, the reservoir 36 and the metering pump 58 may also include a moving platform (not shown), which permits the reservoir, the metering pump and the nozzle 38 to move across the mandrels 22a–22f in the direction of arrow as shown in FIG. 3. The reservoir, the metering pump and the nozzle are displaced in a direction perpendicular to a longitudinal axis 48 of the cylindrical mandrels while the mandrels are stationary and rotated around their longitudinal axes. Wave molding can also be accomplished by simply lowering the rotating mandrel into the wave and allowing it to dwell for a specified time then raising it out of the wave.

The polymer material used to coat the mandrel can be any suitable material having a liquid state while contained in the reservoir of the wave molding apparatus, yet adheres to a mandrel passing through the wave. Preferably, a plastisol, such as polyvinyl chloride, having one or more of the following properties is used: flexible, clear/transparent, biocompatible, non-DEHP/DOP, has a durometer range of 60 Shore A to 60 Shore D, and/or is stable of over time (no discolorization or plastizer leaching). Other polymer material solutions such as organisol, silicone, ridgisol, and urethanes are also believed to be suitable.

A controller 68 is provided for the pump 58 to control the wave and wave height. The controller also can control the lathe for rotation of the mandrel and any transporting device that provides the relative movement between the mandrel and the wave molding apparatus. The controller can also be connected to the heater for the reservoir and the heater for the mandrel to regulate temperature. Such a controller can be readily designed by those skilled in the art taking into consideration the size, shape, and physical characteristics of the cannulae desired to be manufactured.

With regard to the equipment described above, a method of making a cannula includes preheating the mandrel 22 utilizing the induction heating coil 26 (FIG. 2). When the induction heating coil passes over the mandrel, the mandrel heats up depending on the amount of current that is passed through the coil. The process allows the mandrel to be preheated in a relatively short period of time. As noted earlier, instead of moving the heater, the mandrel can be moved with respect to the heater. Furthermore, depending on the properties of the polymer material, no preheating step may be needed.

Next, an initial coat of the plastisol material 40 is applied to the mandrel 22 using the wave molding apparatus 32 (FIGS. 3 and 4). A primer may also be applied before applying the initial coat of polymer material. The polymer material or primer is selected depending on the type of cannula that is being produced.

The metering pump 58, such as a gear metering pump, applies sufficient pressure to raise the plastisol in the reservoir 36 up through the nozzle 38 and over the walls 48 of the nozzle to create a contact with the rotating mandrel, which is rotated at a predetermined speed depending on the wall thickness desired for the cannula to be produced. The mandrel and the wave molding apparatus are moved relative to each other to place the mandrel in contact with the wave over a predetermined length of the mandrel for a predetermined time period.

Figure 6:
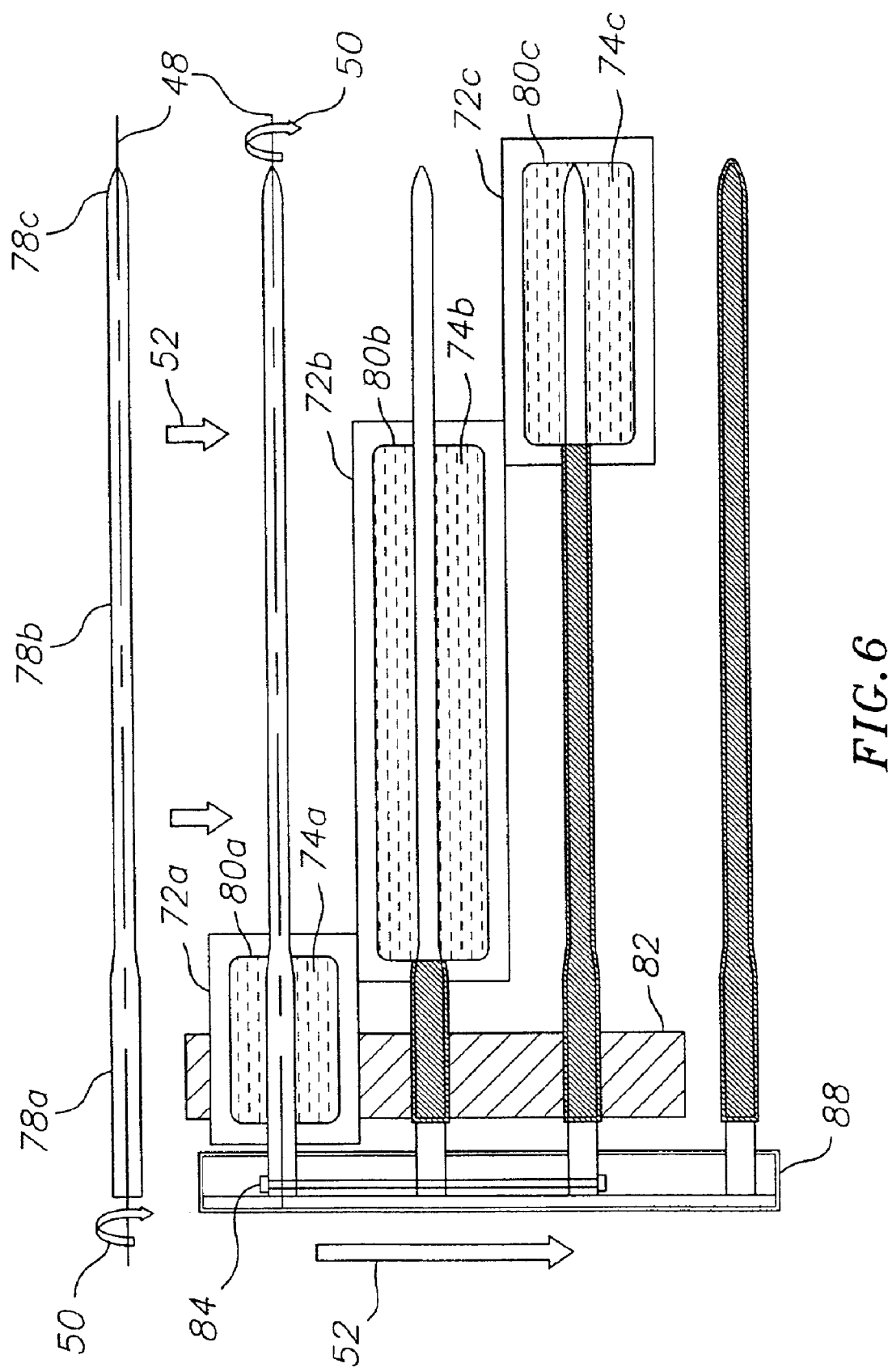
FIG. 6 is a schematic representation of an apparatus for use in the present invention depicting multiple reservoirs and multiple nozzles.

After the rotating mandrel is passed through the wave, the initial coat of polymer material that is adhered to the mandrel is cured. In one embodiment, the curing is accomplished utilizing the heater depicted in FIG. 2. Alternatively, the curing may include simply allowing sufficient time for the polymer material to harden. In some cases, depending on the properties of the polymer material, curing is not required. The above steps may be repeated as desired to attain the desired wall thickness of the cannula. The cannula is then stripped from the mandrel by methods known in the art, such as by forcing compressed air between the mandrel and the cannula, which slightly expands the cannula so that it can be slid off the mandrel. With reference to FIG. 6, multiple reservoirs and multiple nozzles, may be used to permit application of polymer material with varying properties instead of a single type of polymer material utilizing a single reservoir and a single nozzle.

The apparatus includes a plurality of reservoirs 72a, 72b, 72c to provide a plurality of polymer material solutions 74a, 74b, 74c with varying properties to manufacture a cannula having multiple sections. A mandrel 78 comprises three sections—an end or handle section 78a, a middle section 78b, and a tip section 78c. Individual nozzles 80a, 80b and 80c are mounted within the individual reservoirs 72a, 72b and 72c respectively. The reservoirs 72a, 72b, 72c include one or more metering pumps 82 to force the polymer material up through the opening of each nozzle. One or more motors 84 rotate the mandrels 78 in a rotational direction 50.

The metering pumps 82 can be individual units coupled to individual reservoirs 72a, 72b, 72c.

The apparatus also includes an actuator 88 to traverse the mandrels 78 as shown by the arrow 52. Each nozzle forces the wave of polymer material solution into contact with one of the sections 78a, 78b, 78c of the mandrel such that substantially the entire length of the mandrel 78 is coated. The nozzles are preferably arranged relative to each other such that polymer material in adjacent reservoirs form an overlap onto the mandrels to ensure that the two adjoining sections of cannulae are fused together to form a seamless joint. Even though the polymer material solution deposited around each section of the mandrel may be different in hardness and color, the basic characteristics of polymer material solutions are the same. Therefore, the deposited polymer material solutions around the different sections of the mandrel, once cured, are fused together forming a seamless cannula. In yet another embodiment, instead of three sections, the mandrel 78 may have two, or more than three sections depending on the cannula that is being produced. Under this scenario, the apparatus 70 may be modified with a corresponding number of reservoirs and nozzles to provide different types of polymer solutions. Alternatively, a single reservoir may be provided that supplies a plurality of nozzles.

The apparatus 70 further includes various other possible features that are described in FIGS. 3 and 4 such as a rail or moving platforms, a controller, and a reservoir heater. The controller controls the motors, pumps, lathes and heaters of the apparatus 70. The controller can also be used for curing. The controller determines the time and duration each section of the cannula is subjected to heat to help achieve various different wall thicknesses for the cannula. For example, certain areas of a cannula with increased wall thickness may require higher heat input for curing purposes. In such a situation, the controller 68 determines the time at which the curing will begin, duration for which the curing will be performed, and the temperature at which the cannula will be subjected to achieve the desired curing.

A final cure occurs utilizing the heater after the final coat has been applied. Once the final cure is completed, the tubular structure is removed and subjected to a set of secondary operations to produce the cannula. The secondary steps include cutting, punching holes, welding, molding, attaching a connector, fusing, marking and/ or painting to make the cannula to a desired specification.

The dimensions of the tubular structure that are produced are varied by regulating at least one of the nozzle, the mandrel, the speed of the motor, the speed of the actuator, thermal energy of the mandrel, and the selection of the polymer material solution. The quality, type and grade of the polymer material are also a factor to be considered based on the type and the application of the cannula.

Figure 7:
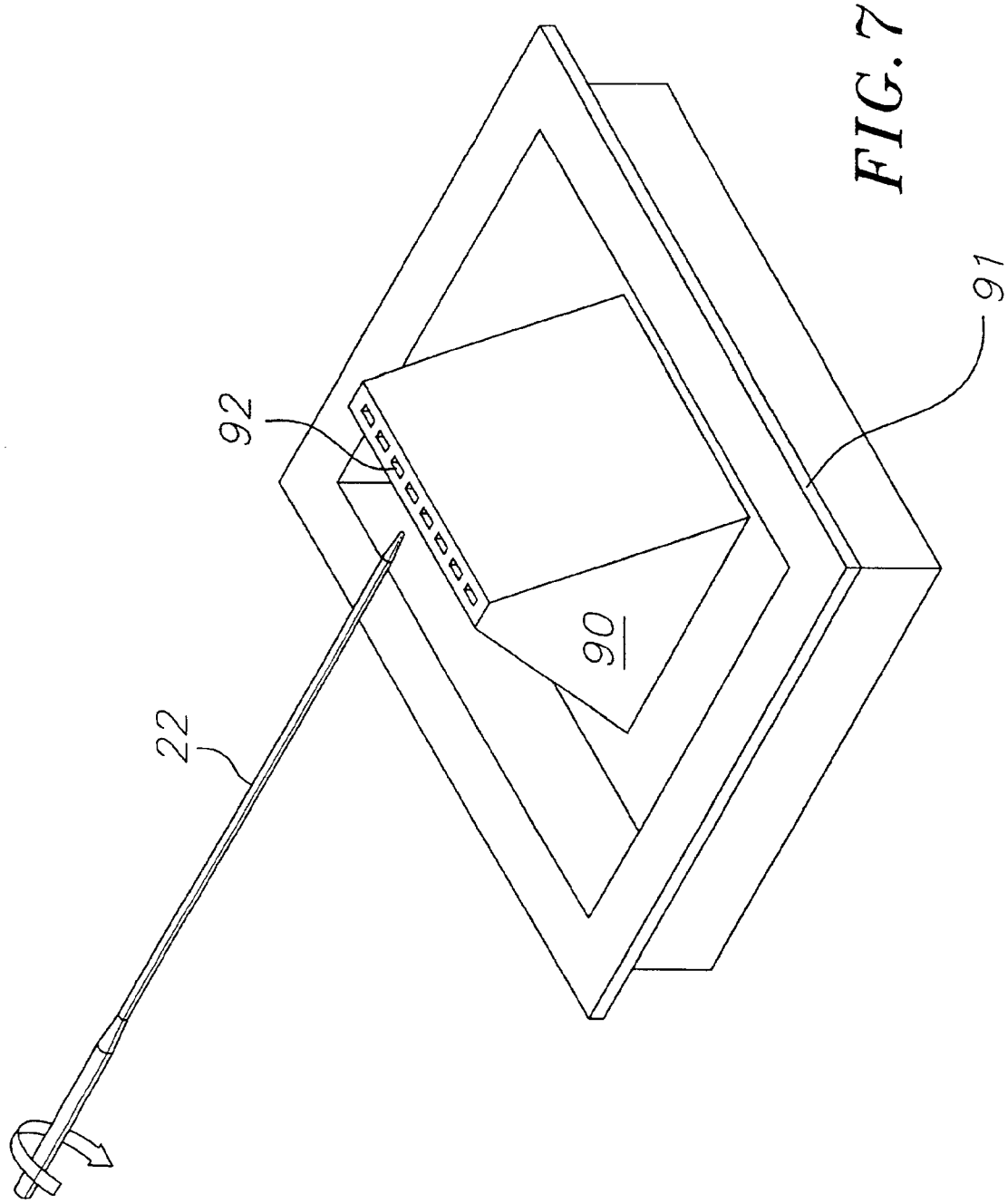
FIGS. 7 through 9 provide different configurations of nozzles and the nozzles' position within the tank in various exemplary positions.
Figure 8:
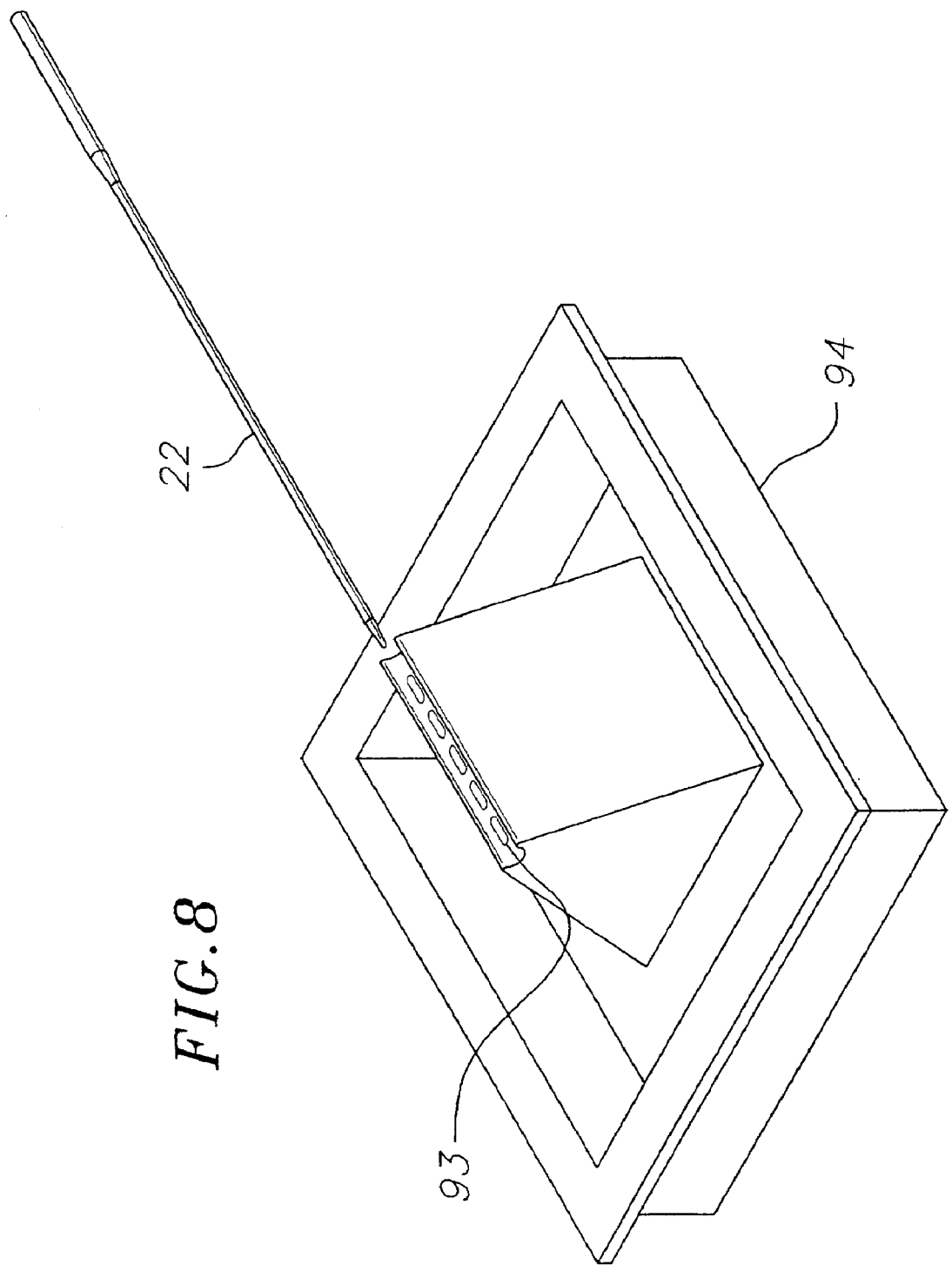
Figure 9:
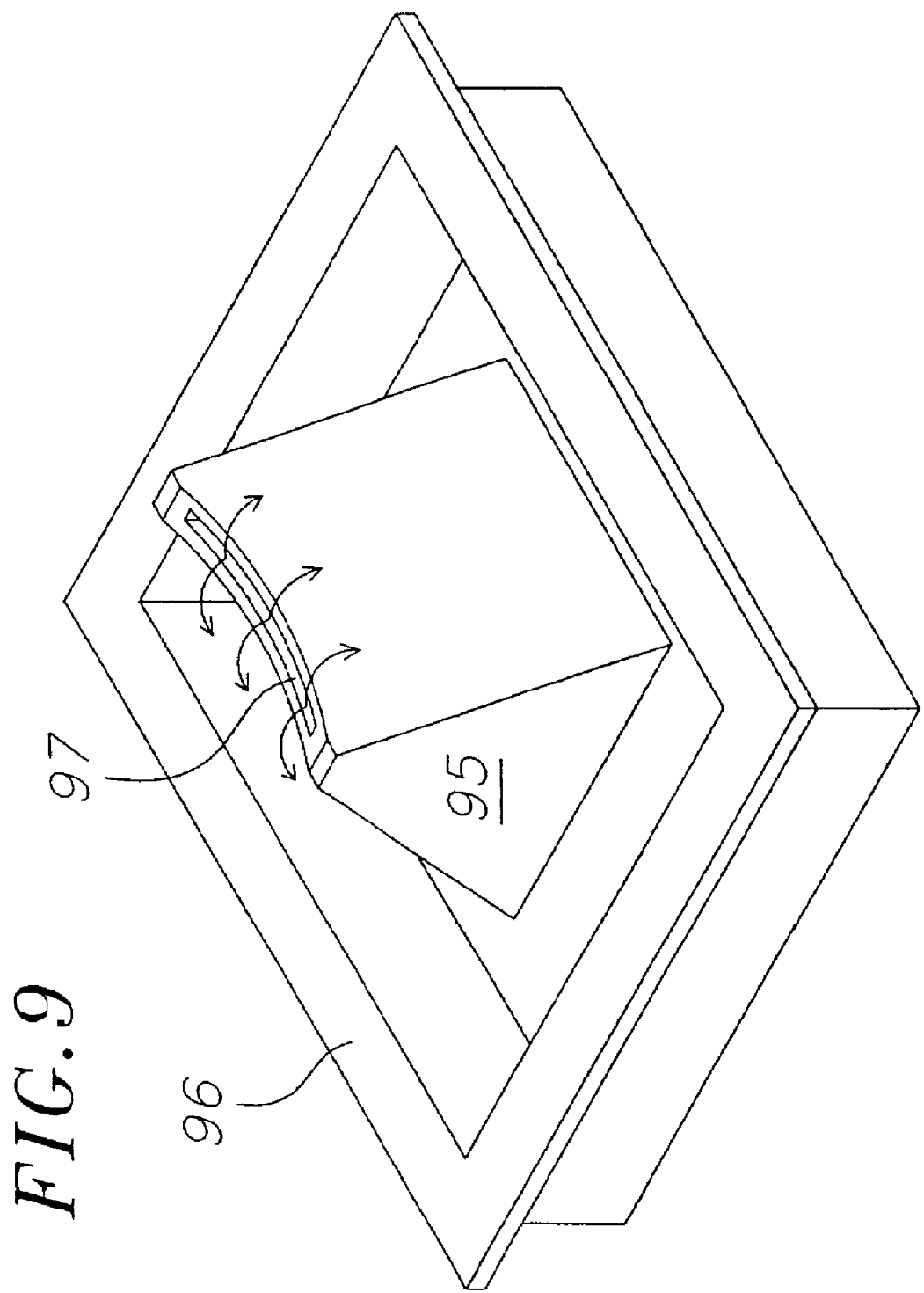

FIGS. 7–9 depict various different nozzle configurations and the nozzles' positions within each respective tank. Different configurations of nozzles are selected based on the mandrel that is being used, the type of the cannula to be produced and control parameters to be applied. As shown in FIG. 7, a "v-shaped" nozzle 90 is raised above the level of a reservoir 91. A pump (not shown) pumps the polymer material up through one or more openings 92 of the nozzle 90. A rotating mandrel 22 is located perpendicular to the nozzle such that one end of the mandrel enters the wave first, coating the mandrel from one end to the other. A plurality of mandrels may also be located side-by-side to enter the wave simultaneously. The nozzle 90 is relatively narrow as compared to the wide (bath) nozzle depicted in FIGS. 3–5. In addition, only a small portion of the mandrel is contacting the wave at any moment compared to the much longer portions of mandrel that are contacting the wave in FIGS. 3–5. Nozzle 90 permits seamless variations of coating thickness along the length of the mandrel.

FIG. 8 is a perspective view of another "v-shaped" nozzle having an elongated semi-circular tip 93 mounted within a reservoir 94. In this case, the mandrel 22 is aligned with the nozzle such that the contour of the mandrel and the contour of the semicircular tip correspond to each other. One end of the mandrel enters the wave first, and proceeds until the mandrel is coated from one end to the other. Alternatively, a rotating mandrel could be lowered into the semicircular tip of the nozzle.

FIG. 9 shows yet another V-shaped nozzle 95 located in a reservoir 96 with a tip having a semi-circular notch 97. The tip is relatively narrow, which, like the nozzle in FIG. 7, provides good control over coating thickness on the mandrel and seamless variations of coating thickness on the mandrel.

The above-described nozzles can be made out of a rigid material such as stainless steel or plastic such as the acetal resin Delrin®. In an alternative embodiment (not shown), the nozzle is mounted outside the reservoir by utilizing separate tubing to carry plastisol from the reservoir to the nozzle. In this embodiment, the excess or overflow plastisol material is directed back into the reservoir by utilizing a return tubing.

Figure 10:
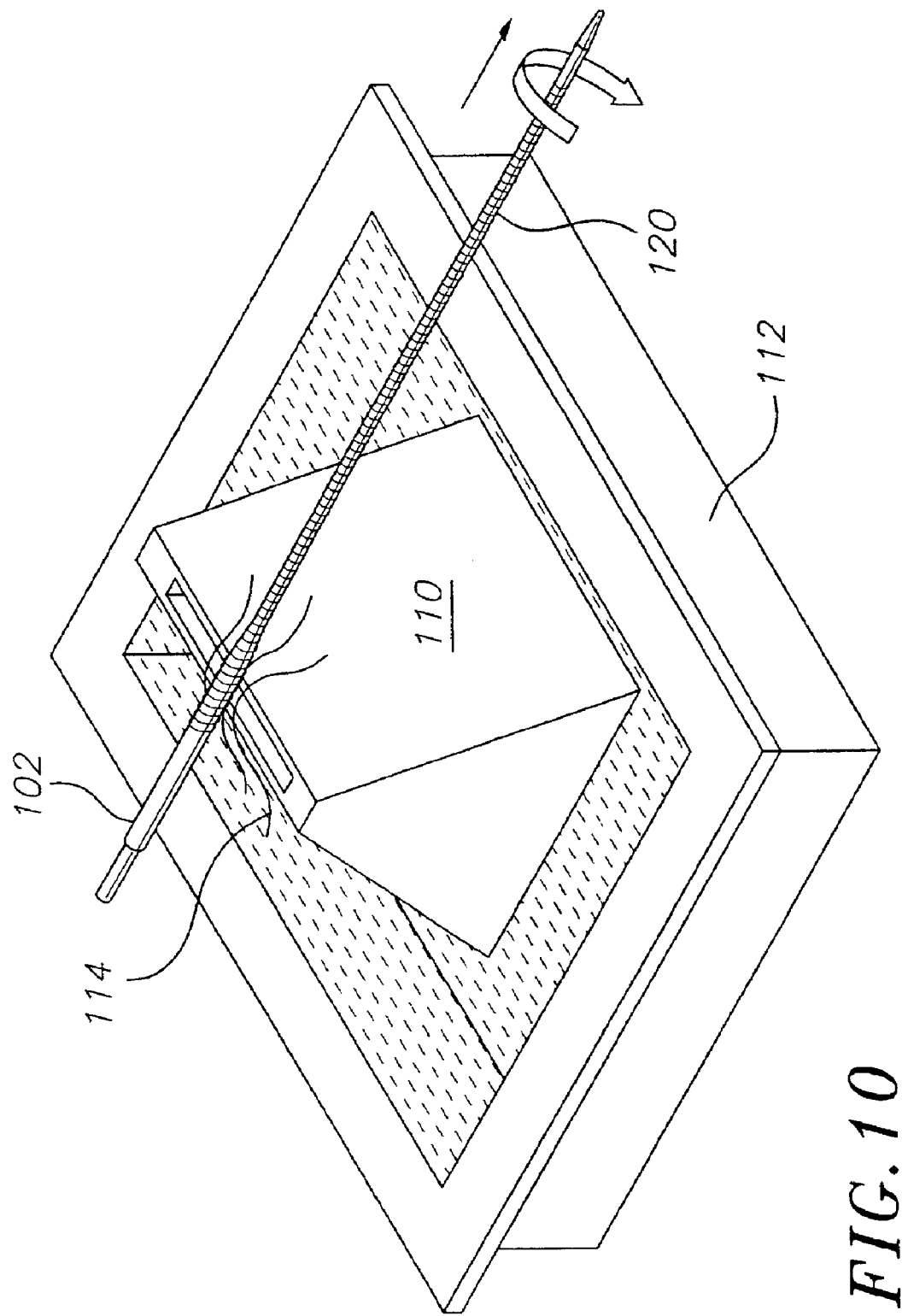
FIG. 10 is a schematic view depicting the wave molding process of the present invention after a spring wire is applied to the mandrel.

In order to obtain a thin-walled flexible cannula that is durable and prevents kinking, it is desirable to incorporate a coil spring into the cannula wall. With reference to FIG. 10, once an initial coat of polymer material has been cured, a coil spring 120 is placed over the coated cylindrical mandrel 102. The spring 120 may be manually inserted over the mandrel 102 or by a mechanical device. As an alternative embodiment, the spring material may be in the form of an unwound wire or flat material and wound around the cylindrical mandrel 102 in a known fashion. Stainless steel is one suitable material for the spring or wire.

The choice of winding per inch for the spring or the diameter or cross-sectional area of the spring material may vary depending upon the desired spring properties and flexibility of the wire reinforced cannulae. For example, a reduced wall thickness for the cannula may be used while maintaining sufficient strength to avoid kinking or bending during handling.

In yet another embodiment, the spring material may be wound around the mandrel or inserted thereover, simultaneously with the application of the plastisol material solution.

Alternatively, instead of a stainless steel or wire spring, a thin walled extruded tube made out of a plastic material is used. The thin walled tube acts as the reinforcement for the cannula to prevent kinking or collapse of the device. The thin walled tubing functions like a reinforced wire and allows the cannula to remain flexible. Also, a spiral thin walled extruded spring made out of a plastic material may be used instead of the extruded tube. The thin walled tube or spiral thin walled extruded spring may be held in place on the mandrel by utilizing methods known in the art. For a given wall thickness, it is preferable that the diameter of the wire spring material is less than the wall thickness to provide a polymer layer along the inner and outer surfaces.

After the spring has been placed on the coated mandrel, a pre-heat step may be used prior to applying a second coat. The second coat or additional coats of polymer material utilizing the wave molding process is applied to the mandrel to yield the desired final diameter. The coat material is selected depending on the type of cannula that is being produced.

A tip of the wire reinforced cannula may be positioned over a second reservoir having a material with different properties. Indeed, as noted above, multiple different polymer material tanks, may be utilized during the cannula manufacturing. Multiple tanks ensure the manufacturing of one cannula with sections having different types of properties.

For areas of the cannulae having an opening for drainage or perfusion, these areas are typically hardened by utilizing higher hardness polymer, or additional hardening steps, or an encapsulated reinforcing material. This ensures that these areas retain sufficient rigidity. Furthermore, during certain medical procedures, some of the areas of the cannula may be clamped. Areas that are clamped are typically non-reinforced. Therefore, it is necessary to have different wall thicknesses to support a specific area of the cannula based on the functionality requirement. The present invention allows the production of a cannula with different wall thicknesses, different hardnesses, reinforcement imbedded within the cannula—all in a single piece product without any bonds, or welds used for assembly. The process further allows production of cannulae with a thinner wall or a small outer diameter for a given inner diameter at substantially less cost than other traditional manufacturing processes such as extrusion and dipping.

It will, of course, be understood that modifications to the present preferred embodiment will be apparent to those skilled in the art. Consequently, the scope of the present invention should not be limited by the particular embodiments discussed above, but should be defined only by the claims set forth below and equivalents thereof.

What is claimed is:

1. A method of making a cannula utilizing wave molding, said method comprising:
   generating a polymer material wave by pumping polymer material up through a nozzle and over a wall of the nozzle to create the wave;
   rotating a mandrel in the polymer material wave to form a coat of polymer material around the mandrel thereby forming a tubular structure; and
   removing the tubular structure from the mandrel.

2. The method of claim 1 further comprising pre-heating the mandrel.

3. The method of claim 1 wherein rotating further comprises:
   rotating the mandrel in the polymer material wave to form an initial coat on the mandrel;
   curing the initial coat;
   depositing a reinforcing material around a selected section of the mandrel;
   rotating the coated mandrel and the reinforcing material in the polymer material wave to form an additional coat of polymer material over the reinforcing material and the initial coat to form the tubular structure; and
   curing the additional coat.

4. The method of claim 3 wherein depositing a reinforcing material further comprises ensuring that the reinforcing material is held in place at the selected section of the mandrel.

5. The method of claim 3 wherein rotating the mandrel further comprises rotating the mandrel at a pre-determined speed in contact with the polymer material wave for a pre-determined period of time.

6. The method of claim 3 further comprising performing at least one of finishing, punching, cutting, joining, connecting, molding, hardening, bending, marking, and painting to the tubular structure.

7. The method of claim 1 further comprising creating holes at pre-determined locations in the tubular structure.

8. The method of claim 2 wherein pre-heating the mandrel comprises pre-heating the mandrel to a pre-determined temperature.

9. The method of claim 3 wherein curing the initial coat comprises curing the initial coat utilizing an induction coil to a pre-determined temperature.

10. The method of claim 3 wherein curing the additional coat comprises curing the additional coat utilizing an induction coil to a pre-determined temperature.

11. A method of making a reinforced cannula utilizing wave molding, said method comprising:
    providing a reservoir containing polymer material and a nozzle wherein the polymer material is pumped from the reservoir up through the nozzle and overflows a wall of the nozzle to generate a polymer material wave;
    pre-heating a mandrel configured to produce a cannula;
    rotating the mandrel in the polymer material wave to form a coat on the mandrel;
    curing the coat;
    depositing a reinforcing material around a selected section of the coated mandrel;
    rotating the coated mandrel and the reinforcing material in the polymer material wave to form an additional coat of the polymer material over the reinforcing material and the coated mandrel to form a reinforced tubular structure;
    curing the additional coat; and
    removing the reinforced tubular structure from the mandrel.

12. The method of claim 11 further comprising punching holes in the tubular structure at pre-determined locations.

13. The method of claim 11 wherein the reinforcing material is a coil spring.

14. A method of making a cannula having a plurality of sections utilizing wave molding, comprising:
    generating a plurality of polymer material waves;
    rotating a mandrel having a plurality of sections and introducing respective ones of the plurality of sections of the mandrel into respective ones of the plurality of polymer material waves to form a tubular structure; and
    removing the tubular structure from the mandrel.

15. The method of claim 14, wherein the respective ones of the plurality of sections of the mandrel are successively introduced into the respective ones of the plurality of polymer material waves.

16. The method of claim 15, further comprising depositing a reinforcing material around a selected section of the mandrel and rotating the selected section of the mandrel over a selected polymer wave thereby forming an additional coat of the polymer material over the reinforcing material.

17. The method of claim 14, wherein a first section of the mandrel is rotated over a first polymer material wave, and a second section of mandrel is rotated over a second polymer material wave and wherein a coating formed on the first section of the mandrel from the first wave and a coating formed on the second section of the mandrel from the second wave overlap.

18. The method of claim 1, wherein the polymer material wave is a flat uniform wave.

19. The method of claim 1, wherein the nozzle is a bath nozzle to permit more than one mandrel to simultaneously contact the wave.

20. The method of claim 1, wherein the nozzle is an elongated nozzle to permit more than one mandrel to simultaneously contact the wave.

21. The method of claim 20, wherein at least one of the mandrel and the elongated mozzle are moved relative to each other in a parallel direction while the mandrel is in the wave.

22. The method of claim 20, wherein at least one of the mandrel and the elongated nozzle are moved relative to each other in a perpendicular direction while the mandrel is in the wave.

23. The method of claim 1, further comprising simultaneously rotating the mandrel and an additional mandrel in the material wave.

24. The method of claim 11, wherein the wall of the nozzle is higher than walls of the reservoir.

25. A method of making a cannula having a plurality of sections utilizing wave molding, comprising:

generating a plurality of separate polymer material waves;

rotating a mandrel having a plurality of sections and introducing respective ones of the plurality of sections of the mandrel into respective ones of the plurality of polymer material waves to form a tubular structure comprising contiguous widths of the separate polymer material on the mandrel;

curing the tubular structure; and removing the tubular structure from the mandrel.

26. The method of claim 25, wherein the respective ones of the plurality of sections of the mandrel are successively introduced into the respective ones of the plurality of separate polymer material waves to form continuous portions of the tubular structure comprising the polymer material of the respective polymer material waves.

* * * * *

UNITED STATES PATENT AND TRADEMARK OFFICE
CERTIFICATE OF CORRECTION

PATENT NO. : 6,936,210 B2  
DATED : August 30, 2005  
INVENTOR(S) : Ross Bartholomew Page 1 of 1

It is certified that error appears in the above-identified patent and that said Letters Patent is hereby corrected as shown below:

Column 11,  
Line 22, after "elongated," delete "muzzle" and insert -- nozzle. --.

Column 12,  
Line 3, before "material wave," insert -- polymer. --.

Signed and Sealed this

First Day of November, 2005

JON W. DUDAS  
*Director of the United States Patent and Trademark Office*